(12) United States Patent
Shikahama (10) Patent No.: US 10,383,757 B2
(45) Date of Patent: Aug. 20, 2019

(54) INGROWN NAIL CORRECTING DEVICE

(71) Applicant: SHIKAHAMA CO., LTD., Adachi-ku (JP)

(72) Inventor: Shigeru Shikahama, Adachi-ku (JP)

(73) Assignee: SHIKAHAMA CO., LTD., Adachi-ku (JP)

( * ) Notice: Subject to any disclaimer, the term of this patent is extended or adjusted under 35 U.S.C. 154(b) by 198 days.

(21) Appl. No.: 14/898,612

(22) PCT Filed: Apr. 9, 2014

(86) PCT No.: PCT/JP2014/060309
§ 371 (c)(1),
(2) Date: Dec. 15, 2015

(87) PCT Pub. No.: WO2015/155856
PCT Pub. Date: Oct. 15, 2015

(65) Prior Publication Data
US 2016/0128862 A1 May 12, 2016

(51) Int. Cl.
*A61F 5/11* (2006.01)
(52) U.S. Cl.
CPC ...................... *A61F 5/11* (2013.01)
(58) Field of Classification Search
CPC .. A61F 5/11; A61F 5/10; A61F 13/063; A61F 13/12; A61F 13/1245; A61F 13/06;
(Continued)

(56) References Cited

U.S. PATENT DOCUMENTS 1,708,716 A * 4/1929 Andersen .................. A61F 5/11
602/31
1,772,130 A * 8/1930 Crenshaw ................. A61F 5/11
602/31
(Continued)

FOREIGN PATENT DOCUMENTS

CN      101873840 A      10/2010
CN      102614039 A      8/2012
(Continued)

OTHER PUBLICATIONS

European Supplementary Search Report dated Apr. 10, 2017 in European Application No. 14889052.8, (8 pages).
(Continued)

*Primary Examiner* — Keri J Nelson
*Assistant Examiner* — Adam Baker
(74) *Attorney, Agent, or Firm* — Oblon, McClelland, Maier & Neustadt, L.L.P.

(57) ABSTRACT

Provide a correcting device capable of being placed onto a nail without applying an excessive force to the nail or of being properly applicable for correcting nails having different sizes.
The correcting device includes a left arm and a right arm, each having an engageable part disposed on a free end so as to be engageable with a side edge of a nail; and a fulcrum member disposed between the left and right arms and having a lower end serving as an abutting part for contact with the nail. The fulcrum member includes a shaft part combined with the base member so as to be vertically movable with respect to the base member by screw movement, a movable member combined with the shaft part so as to be vertically movable with respect to the shaft part and having the abutting part under the shaft part, and an urging member interposed between the shaft part and the movable member so as to urge the movable member. The abutting part extends (Continued)

in left and right directions and has projections disposed on left and right edges such that the projections are adapted to be abutted against the nail while the abutting part is not abutted against the nail between the left and right projections.

14 Claims, 7 Drawing Sheets

(58) Field of Classification Search
CPC ...... A61F 5/019; A61F 5/0195; A61F 5/0111; A61F 15/008; A61B 5/449; A45D 29/00; A45D 29/02; A45D 29/04; A45D 29/06; A43B 3/16; A61G 13/12; A61G 13/1245; A61G 2013/0063
USPC .................................................... 602/31, 30
See application file for complete search history.

(56) References Cited

U.S. PATENT DOCUMENTS

| | | | | |
|---|---|---|---|---|
| 1,917,794 | A * | 7/1933 | Brown ...................... | A61F 5/11 132/73 |
| 2,024,412 | A * | 12/1935 | Wilson ...................... | A61F 5/11 602/31 |
| 2,357,323 | A * | 9/1944 | Goldberg ............ | A61F 5/05866 602/21 |
| 2,613,667 | A | 10/1952 | Stanley | |
| 2,667,917 | A * | 2/1954 | Dustin ................. | A61H 1/0218 297/411.1 |
| 3,299,887 | A * | 1/1967 | Czap ......................... | A61F 5/10 602/21 |
| 4,517,966 | A * | 5/1985 | von Othegraven .. | A61H 1/0218 482/122 |
| 7,628,741 | B2 * | 12/2009 | Adcock ............ | A63B 21/00185 482/122 |
| 8,882,691 | B2 | 11/2014 | Ogawa | |
| 2009/0139071 | A1 | 6/2009 | Palka | |
| 2010/0137771 | A1 * | 6/2010 | Harada ...................... | A61F 5/11 602/31 |
| 2010/0262057 | A1 * | 10/2010 | Chandrasekar ..... | A61F 5/05875 602/22 |
| 2011/0257570 | A1 * | 10/2011 | Erdogan ................... | A61F 5/11 602/31 |
| 2012/0197172 | A1 | 8/2012 | Ogawa | |
| 2012/0284982 | A1 | 11/2012 | Chen et al. | |

FOREIGN PATENT DOCUMENTS

| | | |
|---|---|---|
| CN | 203483556 U | 3/2014 |
| EP | 2 025 309 A1 | 2/2009 |
| JP | 2012 513819 | 6/2012 |
| JP | 5311320 | 10/2013 |
| RU | 41402 U1 | 10/2004 |
| RU | 2492826 C1 | 9/2013 |
| UA | 87538 U | 2/2014 |
| WO | 2008 142880 | 11/2008 |

OTHER PUBLICATIONS

International Search Report dated Jun. 10, 2014 in PCT/JP2014/060309 filed Apr. 9, 2014.
Combined Chinese Office Action and Search Report dated Sep. 14, 2016 in Patent Application No. 201480027797.2 (with English translation of categories of cited documents).
Russian Office Action for RU 2016102717/14, dated Feb. 2, 2018. English Translation provided.
Combined Office Action and Search Report dated Aug. 2, 2018 in Chinese Patent Application No. 201610907774.1 With English translation of categories of cited documents, citing documents AA, AO-AP therein, 6 pages.

* cited by examiner

INGROWN NAIL CORRECTING DEVICE

TECHNICAL FIELD

The present invention relates to an improved correcting device to be used for the purpose of being placed onto a nail in an ingrown nail state to correct the nail to a normal state.

BACKGROUND ART

Although the treatment for an ingrown nail is classified into one performed by an operation and one carried out by correction, the latter has been mainly carried out.

As the correcting device for performing such correction, there have been known devices that are configured to have hooks disposed at both left and right ends of a base plate so as to be engageable with the side edges of a nail such that the vertical distance between the base plate and the hooks is variable by screw arrangement (see Patent Documents 1 and 2).

These conventional measures have been ones that directly apply a correcting force to a nail by operating the screw arrangement and that come off from the nail when the ingrown nail has been corrected to some degree by the application of such a correcting force. Further, the distance between the left and right hooks is variable only in a certain range in Patent Document 1 while the distance is invariable in Patent Document 2. For these reasons, these conventional measures have been difficult to use a single correcting device for correcting nails having different lengths in left and right directions, in other words, different sizes, different thicknesses or different degrees of deformation.

PRIOR ART DOCUMENTS

Patent Documents

Patent Document 1: U.S. Pat. No. 1,708,716
Patent Document 2: U.S. Pat. No. 1,772,130

DISCLOSURE OF INVENTION

Technical Problem

The main problem to be solved by the present invention is that such an ingrown nail correcting device is made to be capable of being placed onto a nail without applying an excessive force to the nail or that a single correcting device can be used so as to be properly applicable for correcting nails having different sizes in left and right directions.

Solution to Problem

In order to overcome the above-mentioned problem, the present invention provides an ingrown nail correcting device including:

a left arm having an engageable part disposed on a free end so as to be engageable with a left side edge of a nail;

a right arm having an engageable part disposed on a free end so as to be engageable with a right side edge of the nail; and a fulcrum member disposed between the left and right arms and having a lower end serving as an abutting part for contact with the nail;

each of the left and right arms having an upper end pivotally combined with a base member;

the fulcrum member including a shaft part combined with the base member so as to be vertically movable with respect to the base member by screw movement, a movable member combined with the shaft part so as to be vertically movable with respect to the shaft part and having the abutting part disposed under the shaft part, and an urging member interposed between the shaft part and the movable member so as to urge the movable member; and the abutting part extending in left and right directions, having projections disposed on left and right edges such that the projections are adapted to be abutted against the nail while the abutting part is not abutted against the nail between the left and right projections.

When in such a state where the engageable part of the left arm is brought into engagement with the left side edge of a nail, and where the engageable part of the right arm is brought into engagement with the right side edge of the nail, operation is made to turn the fulcrum member in the internally thread hole downward from a placing state where the abutting part of the fulcrum member is abutted against the nail, the movable member is moved upward with an urging force being stored in the spring. Because the spring applies a force to the base member so as to move the base member away from the nail, i.e. to generate a force in a direction to expand the distance between the engageable part of the left arm and the engageable part of the right arm, the correcting device can apply a force to the nail in a direction to correct the ingrown nail. Because such a force is given by the urging member, the correcting device can be placed onto the nail without an excessive force being applied to the nail. When the ingrown nail starts to be corrected, the left side edge and the right side edge of the nail are lifted to expand the distance between both side edges. Although the lifting allows the distance between the base member and the nail to expand while the movable member is gradually moved downward to gradually decrease the urging force of the urging member acting on the nail, the correcting device does not come off from the nail. Because the correcting device thus configured applies the force to the nail by the left arm and the right arm having the respective engageable parts, the correcting device can be placed onto the nail as described above without being affected by the size of the nail, the thickness of the nail and the degree of deformation in the nail.

The abutting part is configured to be abutted against the nail at the left and right projections while being brought out of contact the nail N at a part thereof between both projections. By this arrangement, the deformation in the left side edge of the nail is corrected between the engageable part of the left arm and the left projection while the deformation in the right side edge of the nail is corrected between the engageable part of the right arm and the right projection. Thus, not only the correcting forces can be collectively applied to the side edges of the nail but also the central part of the nail can be prevented from being subjected to unnecessary deformation.

The correcting device may be configured to include at least two different abutting structures as the abutting part and having different lengths in the left and right directions. When the correcting device is configured thus, one of the abutting structures may be chosen as the optimum one, taking into account the width of an ingrown nail to be corrected, and be fitted to a main body of the movable member to properly correct the ingrown nail.

Advantageous Effects of Invention

The ingrown nail correcting device according to the present invention can be placed onto a nail without applying an excessive force to the nail or be properly used to correct nails having different sizes in left and right directions in despite of being formed even in a single device.

DESCRIPTION OF EMBODIMENTS

Now, a typical embodiment of the present invention will be described in reference to FIGS. 1 to 7. The correcting device S according to this embodiment may be used for the purpose of being placed onto a nail N in an ingrown nail state to correct the nail to a normal state.

The correcting device S according to this embodiment includes a base member 1, a left arm 2, a right arm 2 and a fulcrum member 3. The correcting device S is typically made of metal or a synthetic resin. In the shown example, an abutting structure 312, which is fitted to a movable member 31 described later, is made of a synthetic resin while the other members of the correcting device are made of metal.

The base member 1 has a pivotal assembling part 10 disposed on a left end to have the left arm 2 pivotally assembled thereto, a pivotal assembling part 10 disposed on a right end to have the right arm 2 pivotally assembled thereto, and an internally threaded hole 11 formed in an intermediate position thereof in left and right directions so as to vertically pass therethrough. In the shown example, the base member 1 is prepared by processing a metal bar member. The pivotal assembling parts 10 are configured to have shaft apertures 10a formed in the left and right end of the bar member so as to pass therethrough in front and rear directions (see FIG. 2).

The left arm 2 has an engageable part 20 disposed on a free end so as to be engageable under a left side edge Na of the nail N. The right arm 2 has an engageable part 20 disposed on a free end so as to be engageable under a right side edge Na of the nail N.

In the shown example, each of the left arm 2 and the right arm 2 is constituted by pivotally combining a forearm part 21 and an upper arm part 22, has the engageable part 20 carried on the forearm part 21, and the upper arm part 22 has an upper end pivotally combined with the base member 1. In the shown example, each of the left arm 2 and the right arm 2 is prepared by processing a metal round bar material.

Figure 1:
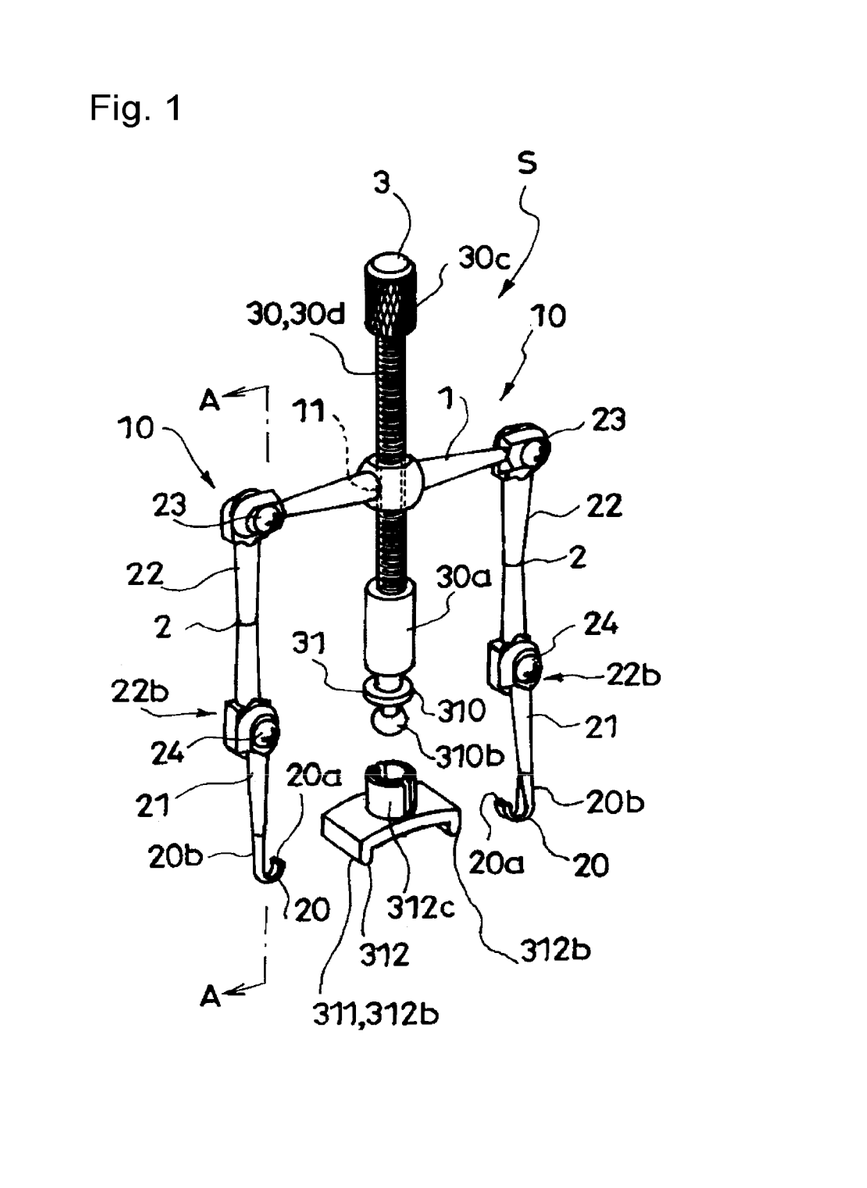
FIG. 1 is a perspective view of the correcting device according to an embodiment of the present invention.
Figure 2:
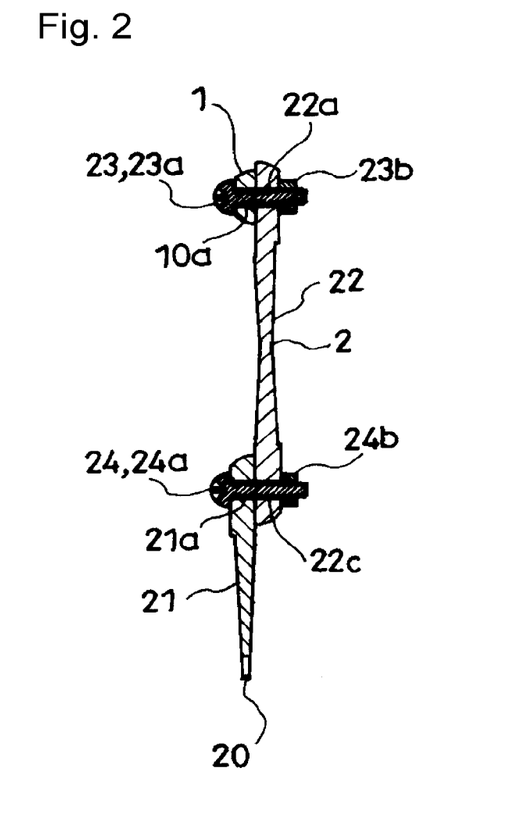
FIG. 2 is a cross-sectional view taking along line A-A of FIG. 1.
Figure 3:
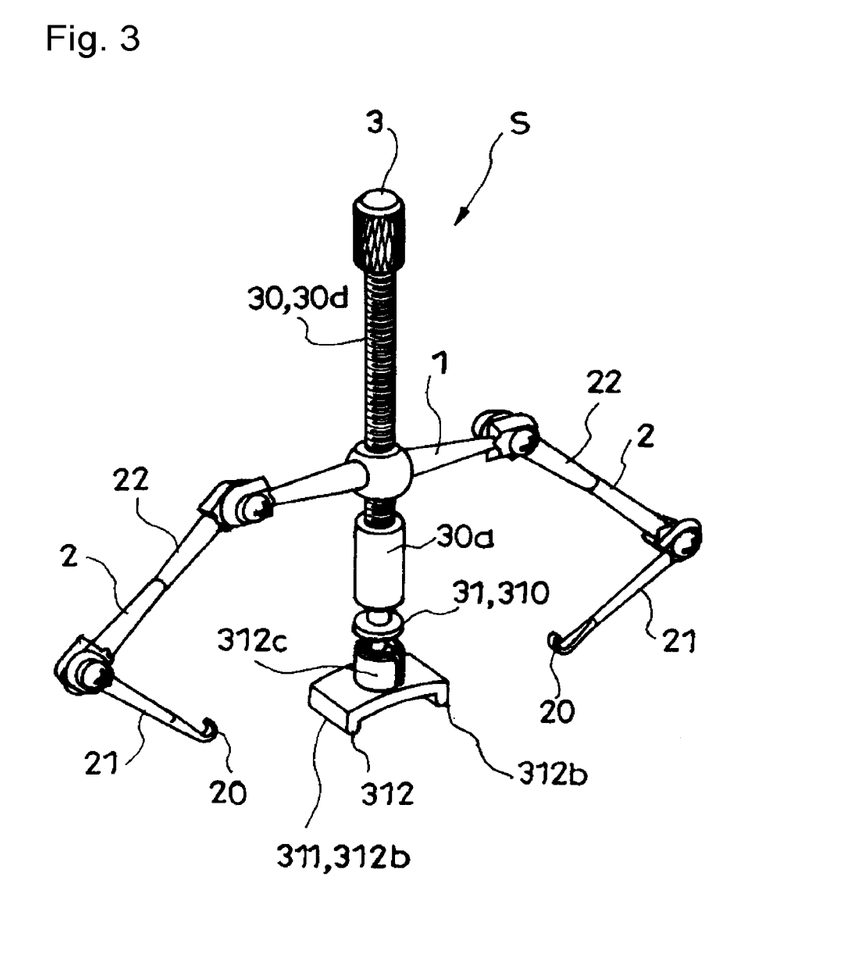
FIG. 3 is a perspective view of the correcting device with both left and right arms being opened.

As shown in FIG. 2, each upper arm 22 has a shaft aperture 22a formed in an upper end so as to pass therethrough in the front and rear directions. Each upper arm 22 is pivotally combined with the base member 1 by passing a screw member 23 through the shaft aperture 22a and the corresponding shaft aperture 10a of the base member 1. Each screw member 23 has a round head 23a formed on one end of a shaft part which is passed through the shaft apertures 10a and 22a. Additionally, each screw member has a nut 23b screwed on the other end of the shaft part. Each upper arm 22 has a pivotal assembling part 22b formed in a lower end so as to assemble the associated forearm 22 thereto. Each pivotal assembling part 22b also has a shaft aperture 22c formed in a lower end of the associated round bar material so as to pass therethrough in the front and rear directions.

As shown in FIG. 2, each forearm 21 also has a shaft aperture 21a formed in an upper end so as to pass therethrough in the front and rear directions. Each forearm 21 is pivotally combined with the associated upper arm 22 by passing a screw member 24 through the shaft aperture 21a thereof and the corresponding shaft aperture 22c of the upper arm 22. Each screw member 24 also has a round head 24a formed on one end of a shaft part which is passed through the shaft apertures 21a and 22c. Additionally, each screw member has a nut 24b screwed on the other end of the shaft part.

The lower end of each forearm 21 is formed so as to have a thickness gradually decreasing toward its distal edge. The lower end of each forearm 21 is formed with the corresponding engageable part 20 such that the corresponding engageable part has a hooking base part 20b integrally connected to the distal edge and is formed in a hook shape bent toward an inner side of the lower end so as to have a hook edge 20a directed upward.

The fulcrum member 3 is disposed between the left arm 2 and the right arm 3 and has a lower end serving as an abutting part 311 with the nail N. The fulcrum member 3 includes a shaft member 30 vertically movably combined with the base member 1 by screw arrangement, the movable member 31 vertically movably combined with the shaft member 30 and having the abutting part 311 disposed under the shaft member 30, and a compressing spring 32 interposed, as an example of the urging member to urge the movable member 31, between the movable member 31 and the shaft member 30.

In the shown example, the shaft member 30 has a lower end formed as a cylindrical part 30a which has an axis coinciding with the central axis of the shaft member 30 and has an open lower end.

The movable member 31 of the fulcrum member 3 is constituted by a main body 310 and the abutting structure 312 detachably fitted to a lower end of the main body 310 so as to provide the abutting part 311.

The main body 310 is formed in a shaft shape so as to have a circular plate-shaped head 310a formed on an upper end and a spherical head 310b formed on a lower end. The main body 310 is inserted in the cylindrical part 30a from a part thereof close to the circular plate-shaped head 310a so as to be vertically movable along the central axis of the shaft member 30. The open lower end of the cylindrical part 30a is formed with an inner flange 30b. The spring 32 is interposed between the circular plate-shaped head 310a and the deepest section of the cylindrical part 30a. The movable member 31 is movable upward against the urging force of the spring 32, from a maximum projecting position where the circular plate-shaped head 310a is brought into engagement with the inner flange 30b.

The abutting structure 312 is elongated in left and right directions and has projections 312b formed on a left edge and a right edge, respectively, such that the abutting structure is configured to be brought into contact with the nail N at the projections 312b while being not brought into contact with the nail N at a portion thereof between the left and right projections 312b and 312b.

In the shown example, the abutting structure 312 is curved so as to have an upper side convexly curved and an lower side concavely curved, and the abutting structure is configured to have the projections 312b and a fitting part 312c for the main body 310 formed on a curved plate part 312a elongating in the left and right directions and having a short width in the front and rear directions.

In the shown example, each of the projections 312b is formed in a rib shape extending along the width direction of the curved plate part 312a so as to downwardly project from a lower side of the curved plate part 312a.

The fitting part 312c is formed in a cylindrical shape so as to have a bottom end of the cylindrical shape joined to the upper side of the curved plate part 312 at a position intermediate in the left and right directions and have a top end of the cylindrical shape opened. The fitting part 312c has an inner diameter size set at the widest size intermediate both ends of the cylindrical shape so as to substantially correspond to the outer diameter of the spherical head 310b while the top end of the cylindrical shape 312d has an inner diameter set so as to be slightly smaller than the outer diameter of the spherical head 310b. The fitting part 312c has slits 312e formed therein on both sides in a diametrical direction thereof so as to extend from the top end of the cylindrical shape 312d in an axial direction of the cylindrical shape. By the provision of the slits 312e, the fitting part 312c is configured to be elastically deformable in a direction to widen the inner diameter. When the spherical head 310b is pressed against the top end 312d of the fitting part 312c, the fitting part 312c is elastically deformed to accept the spherical head 310b. When the spherical head 310b is entirely accepted in the fitting part 312c, the fitting part 312c is elastically returned to the original shape. Thus, the abutting structure 312 is configured to be detachably fitted to the lower end of the main body 310. The abutting structure 312 is configured so as to be pivotable around the entire circumference of the central axis (axis of the cylindrical shape) of the main body 310 such that the abutting structure 312 can be swingably adjusted to bring a state where the abutting part 311 is properly brought into contact with the nail N.

The shaft member 30 has an upper end formed with a knurled part 30c which has a knurling formed thereon along the central axis of the shaft member 30. The shaft member 30 has an externally threaded part 30d formed thereon between the knurled part 30c and the cylindrical part 30a so as to be engageable with the internally threaded hole 11 of the base member 1 such that the fulcrum member 3 is combined with the base member 1 by screwing the externally threaded part 30d of the shaft member 30 in the internally threaded hole 11 of the base member 1. In other words, the knurled part 30c of the fulcrum member 3 is located above the base member 1 while the abutting part 311 is located under the base member 1.

Figure 4:
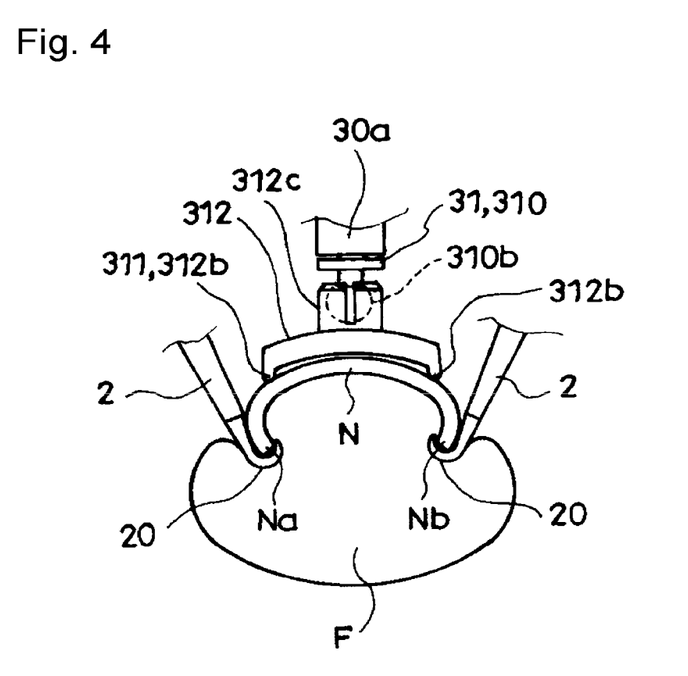
FIG. 4 is a schematic front view of essential parts of the correcting device, showing a state where the correcting device is placed, seen from the tip side of a toe.
Figure 5:
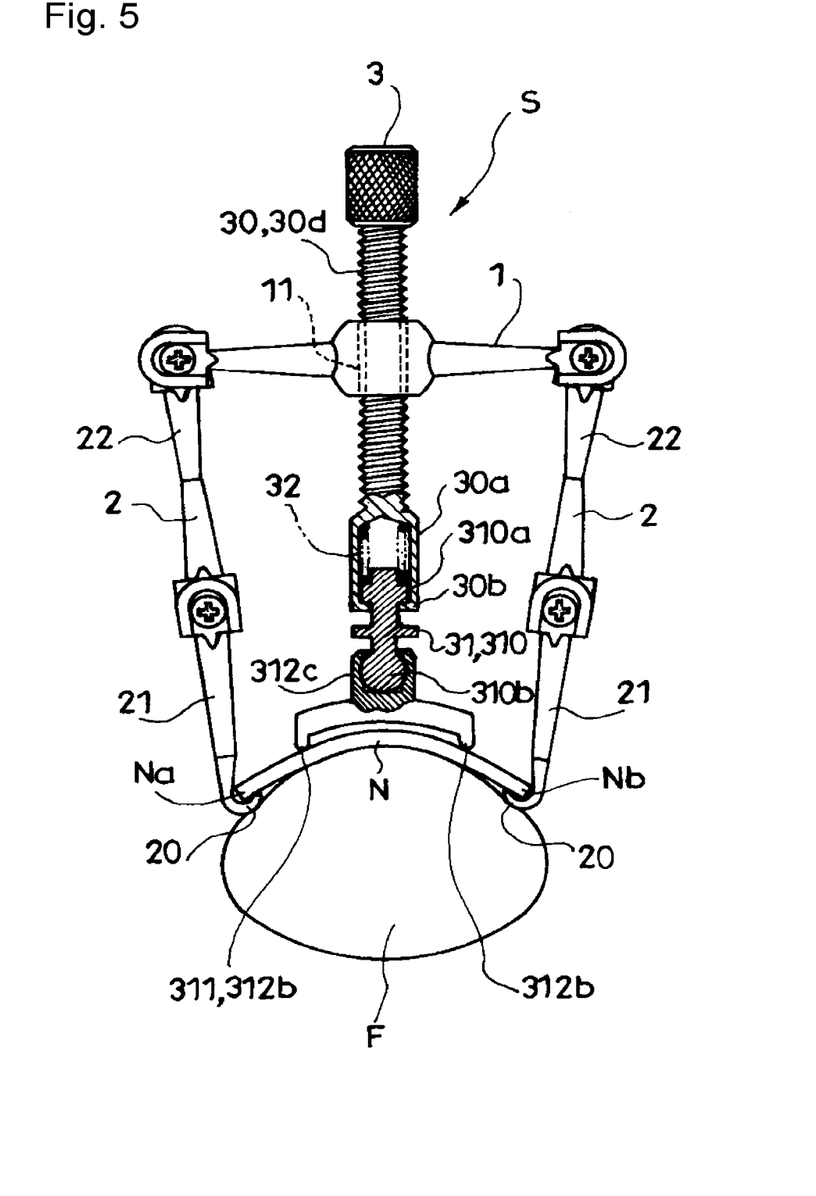
FIG. 5 is a schematic front view of the correcting device with essential parts thereof shown in section, showing a state where the correcting device is placed, and an ingrown nail has been corrected.

When in such a state where the engageable part 20 of the left arm 2 is brought into engagement with the left side edge Na of the nail N while the engageable part 20 of the right arm 2 is brought into engagement with the right side edge Nb of the nail N, operation is made to turn the fulcrum member 3 in the internally thread hole downward from a placing state where the abutting part 311 of the fulcrum member 3 is abutted against the nail N, the movable member 31 is moved upward with an urging force being stored in the spring 32 (see FIG. 4 where symbol F indicates the toe). Because the spring 32 applies a force to the base member 1 so as to move the base member away from the nail N, i.e. to generate a force in a direction to expand the distance between the engageable part 20 of the left arm 2 and the engageable part 20 of the right arm 2, the correcting device S can apply a force to the nail N in a direction to correct the ingrown nail. Because such a force is given by the spring 32, the correcting device can be placed onto the nail N without an excessive force being applied to the nail N. When the ingrown nail starts to be corrected, both left side edge Na and right side edge Nb of the nail N are lifted to expand the distance between both side edges. Although the lifting allows the distance between the base member 1 and the nail N to expand while the movable member 31 is gradually moved downward to gradually decrease the urging force of the spring 32 acting on the nail N, the correcting device S does not come off from the nail N (see FIG. 5). Because the correcting device S applies the force to the nail N by the left arm 2 and the right arm 2 having the respective engageable parts 20, the correcting device can be placed onto a nail N as described above without being affected by the size of the nail N, the thickness of the nail N and the degree of deformation in the nail N. In addition to a case where both side edges of a nail N are equally curved and deformed as shown in FIG. 4, it is not an uncommon case that one of both side edges of a nail N in an ingrown nail has a greater deformation than the other side edge. Even in a case where the left and right side edges are not equal in deformation, the correcting device S can be placed onto such a nail N without trouble in a state to bring the contact position of the abutting part 311 of the fulcrum member 3 close to the side edge having a greater deformation. This is because each of the left arm 2 and the right arm 2 is constituted by a forearm 21 and an upper arm 22 pivotally combined so as to be bendable in the shown example. Thus, it is possible to correct an ingrown nail effectively even in the latter case.

Although being not shown, each of the left arm 2 and the right arm 2 may be constituted by a single bar-shaped material having an upper end pivotally combined with the base member 1 and a lower end formed with an engageable part 20.

Typically, the fulcrum member 3 is threadably advanced from such a state to place the correcting device S onto nail N as described above within a range where the force applied to the nail N does not become too excessive. In this state, the foot is immersed in hot water to make the nail N easily deformable. When the ingrown nail is corrected to some degree and the urging force of the spring 32 is attenuated to decrease the force applied to the nail N, correction can be continued by further advancing the fulcrum member 3 threadably as required.

Figure 8:
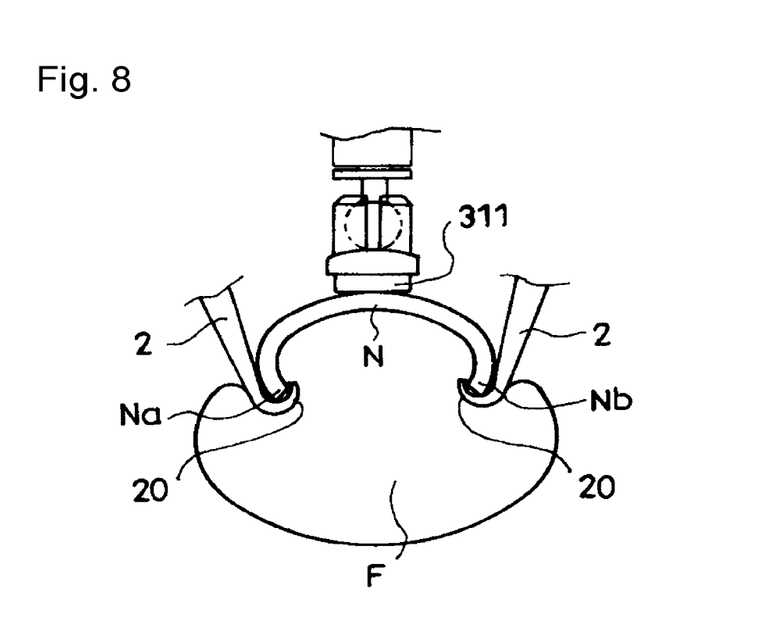
FIG. 8 is a schematic front view showing essential parts of a comparative example.
Figure 9:
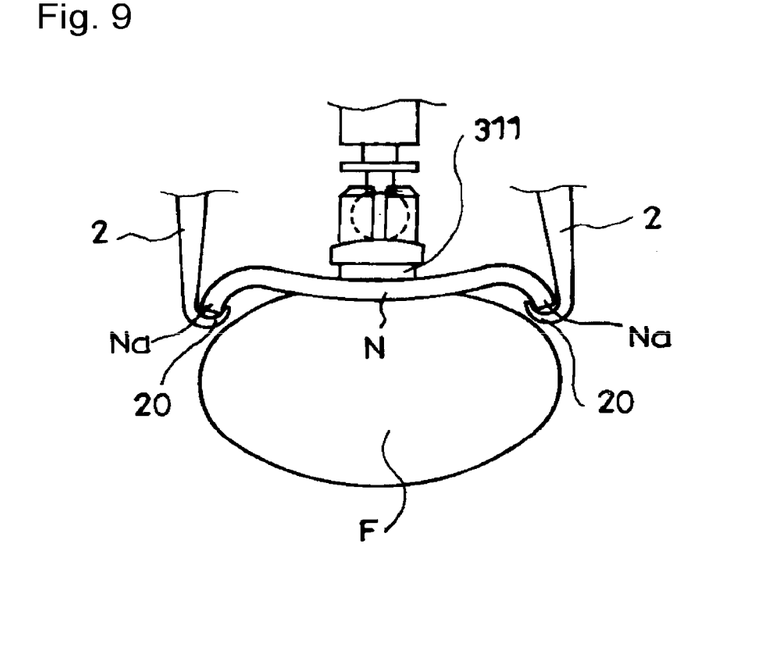
FIG. 9 is a schematic front view showing the essential parts of the comparative example.

When the abutting part 311 of the correcting device S is simply pressed against a central portion of a nail N shown in FIG. 8, the correcting forces are difficult to be concentrated on the side edges Na and Nb of the nail N in some times because the central portion is sunk while the abutting part 311 is away from both side edges Na and Nb of the nail N as shown in FIG. 9.

In this regard, in the correcting device S according to this embodiment, the abutting part 311 is configured to be abutted against the nail N at the left and right projections 312b and 312b while being brought out of contact the nail N at a part thereof between both projections. By this arrangement, the deformation in the left side edge Na of the nail N is corrected between the engageable part 20 of the left arm 2 and the left projection 312b while the deformation in the right side edge Nb of the nail N is corrected between the engageable part 20 of the right arm 2 and the right projection 312b. Thus, not only the correcting forces can be collectively applied to the side edges Na and Nb of the nail N but also the central part of the nail N can be prevented from being subjected to unnecessary deformation.

Figure 6:
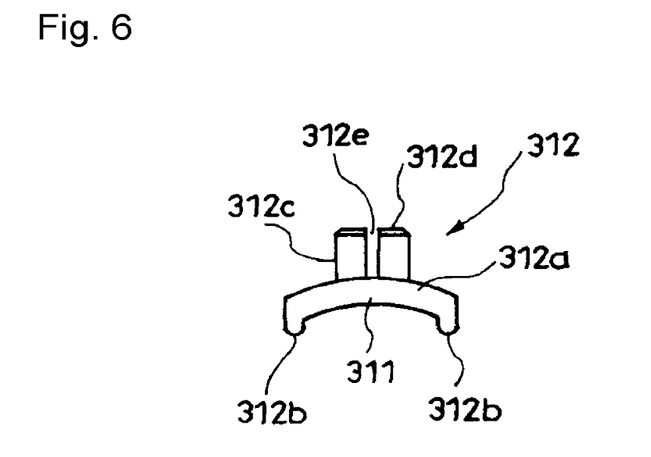
FIG. 6 is a schematic front view showing one of a plurality of different abutting structures constituting the correcting device.
Figure 7:
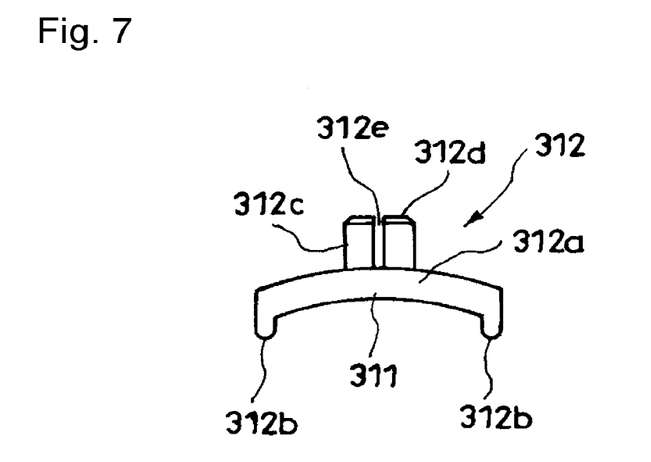
FIG. 7 is a schematic front view showing another one of the different abutting structures constituting the correcting device.

Furthermore, in this embodiment, the correcting device S may include at least two different abutting structures 312, 312 having different lengths in the left and right directions as shown in FIGS. 6 and 7. One of the abutting structures may be chosen as the optimum one, taken into account the width of a nail N to be corrected, and be fitted to the main body 310 of the movable member 31 to properly correct the ingrown nail.

The present invention should not be construed as being limited to the embodiment described above and embrace all embodiments capable of attaining the object of the present invention.

The invention claimed is:

1. An ingrown nail correcting device comprising:
a base member;
a left arm having an engageable part disposed on a free end so as to engageable with a left side edge of a nail;
a right arm having an engageable part disposed on a free end so as to be engageable with a right side edge of the nail; and
a fulcrum member disposed between the left and right arms and having a lower end serving as an abutting part for abutting against the nail;
each of the left and right arms having an upper end pivotally combined with the base member;
the fulcrum member including a shaft part with external threads, the base member including a threaded hole engaged with the external threads of the shaft part of the fulcrum member so as to be vertically movable with respect to the base member by screw movement,
the fulcrum member including a movable member combined with the shaft part so as to be vertically movable with respect to the shaft part, the movable member including a spherical head at a lower end, and the abutting part includes a fitting part to receive the spherical head of the movable member therein such that the abutting part is pivotable around a central axis of the movable member, and an urging member interposed between the shaft part and the movable member so as to urge the movable member; and
the fulcrum member including a plate having a top face and a bottom face, the top and bottom face being connected by an edge extending around a perimeter of the plate, the edge including a front portion, a rear portion opposite to the front portion, a left portion connecting a left side of the front portion to a left side of the rear portion, and a right portion opposite to the left portion and connecting a right side of the front portion to a right side of the rear portion,
the fulcrum member including a left projection disposed along the left portion of the edge and extending from the left side of the front portion to the left side of the rear portion and a right projection disposed along the right portion of the edge and from the right side of the front portion to the right side of the rear portion and extending the left and right projections project downwardly from the bottom face of the plate such that the left and right projections are adapted to be abutted against the nail while the abutting part is not abutted against the nail between the left and right projections,
wherein the shaft part includes a cylindrical part formed on a lower end of the shaft part, a lower end of the cylindrical part is open, and a main body of the movable member is inserted in the cylindrical part, and
wherein the urging member is positioned within the cylindrical part of the shaft part and above a top of the movable member so as to urge the movable member away from the shaft part.

2. The correcting device according to claim 1, wherein the movable member comprises a main body and an abutting structure, the abutting structure being detachably fitted to a lower end of the main body so as to constitute the abutting part.

3. The correcting device according to claim 1, wherein the movable member comprises a main body and at least two different abutting structures, each of the at least two different abutting structures being configured to be detachably fitted to a lower end of the main body so as to constitute the abutting part, each of the at least two different abutting structures having different lengths in the left and right directions.

4. The correcting device according to claim 1, wherein the plate is curved such that the bottom face of the plate is concave.

5. The correcting device according to claim 1, wherein the left arm includes an upper arm part pivotally attached to the fulcrum member and a forearm part pivotally attached to the upper arm part.

6. The correcting device according to claim 5, wherein the engageable part is disposed on the forearm part.

7. The correcting device according to claim 5, wherein the forearm part is pivotally attached to the upper arm part by a screw passing through an aperture in the forearm part and an aperture in the upper arm part.

8. The correcting device according to claim 1, wherein the open lower end of the cylinder part includes an inner flange, and the movable member includes a circular head at an upper end of the movable member, the circular head of the movable member being positioned within the cylinder part and brought into engagement with the inner flange by the urging member.

9. An ingrown nail correcting device comprising:
a base member;
a left arm having an engageable part disposed on a free end so as to engageable with a left side edge of a nail;
a right arm having an engageable part disposed on a free end so as to be engageable with a right side edge of the nail; and
a fulcrum member disposed between the left and right arms and having a lower end serving as an abutting part for abutting against the nail;
each of the left and right arms having an upper end pivotally combined with the base member;
the fulcrum member including a shaft part combined with the base member so as to be vertically movable with respect to the base member by screw movement, the abutting part being disposed under the shaft part; and
the fulcrum member including a plate having an upper face and a lower face, the upper face and lower face being connected by an edge extending around a perimeter of the plate, the edge including a front portion, a rear portion opposite to the front portion, a left portion connecting a left side of the front portion to a left side of the rear portion, and a right portion opposite to the left portion and connecting a right side of the front portion to a right side of the rear portion, the fulcrum member including a left projection disposed along the left portion of the edge and extending from the left side of the front portion to the left side of the rear portion and a right projection disposed along the right portion of the edge and extending from the right side of the front portion to the right side of the rear portion and the left and right projections project downwardly from the lower face of the plate and having a rib shape, and the lower face of the plate forms a concave shape extending continuously and without additional projections between the left and right projections such that the projections are adapted to be abutted against the nail while the abutting part is not abutted against the nail between the left and right projections.

10. The correcting device according to claim 9, wherein the plate is curved such that the bottom face of the plate is concave.

11. The correcting device according to claim 9, wherein the left arm includes an upper arm part pivotally attached to the fulcrum member and a forearm part pivotally attached to the upper arm part.

12. The correcting device according to claim 11, wherein the engageable part is disposed on the forearm part.

13. The correcting device according to claim 11, wherein the forearm part is pivotally attached to the upper arm part by a screw passing through an aperture in the forearm part and an aperture in the upper arm part.

14. An ingrown nail correcting device comprising:
a base member;
a left arm having an engageable part disposed on a free end so as to engageable with a left side edge of a nail;
a right arm having an engageable part disposed on a free end so as to be engageable with a right side edge of the nail; and
a fulcrum member disposed between the left and right arms and having a lower end serving as an abutting part for abutting against the nail;
each of the left and right arms having an upper end pivotally combined with the base member;
the fulcrum member including a shaft part combined with the base member so as to be vertically movable with respect to the base member by screw movement, the abutting part being disposed under the shaft part; and
the fulcrum member including a plate having an upper face and a lower face, the upper face and lower face being connected by an edge extending around a perimeter of the plate, the edge including a front portion, a rear portion opposite to the front portion, a left portion connecting a left side of the front portion to a left side of the rear portion, and a right portion opposite to the left portion and connecting a right side of the front portion to a right side of the rear portion, and the fulcrum member including a left projection disposed along the left portion of the edge and extending from the left side of the front portion to the left side of the rear portion and a right projection disposed along the right portion of the edge and extending from the right side of the front portion to the right side of the rear portion and the left and right projections project downwardly from the lower face of the plate and having a rib shape, and the lower face of the plate forms a shape extending continuously and without additional projections between the left and right projections such that the projections are adapted to be abutted against the nail while the abutting part is not abutted against the nail between the left and right projections.

* * * * *